United States Patent
Staller et al.

[11] Patent Number: 5,626,099
[45] Date of Patent: May 6, 1997

[54] THERAPEUTIC GROOMER

[76] Inventors: Gregory S. Staller, 15 Sawmill Rd., Lebanon, N.J. 08833; Linda K. Tucker, P.O. Box 885 Lower Hollow Rd., Dorset, Vt. 05251

[21] Appl. No.: 517,098

[22] Filed: Aug. 21, 1995

[51] Int. Cl.⁶ .................................................. A01K 13/00
[52] U.S. Cl. ............................ 119/625; 119/600; 600/9
[58] Field of Search .................... 119/83, 85, 86, 119/92, 93; 600/9, 15; 209/636; 335/302, 303

[56] References Cited

U.S. PATENT DOCUMENTS

| | | |
|---|---|---|
| 238,444 | 3/1881 | Scott . |
| 259,574 | 6/1882 | Murdock ................................ 335/302 |
| D. 290,654 | 6/1987 | Ohnishi ................................ D24/206 |
| 429,010 | 5/1890 | Burke ................................... 119/85 |
| 675,527 | 6/1901 | Righter et al. . |
| 2,238,603 | 4/1941 | Runnels ............................... 119/85 X |
| 2,988,049 | 6/1961 | Bean ..................................... 119/83 |
| 3,107,665 | 10/1963 | Nordgren ............................. 119/83 |
| 4,266,533 | 5/1981 | Ryaby et al. ......................... 600/14 |
| 4,343,265 | 8/1982 | Belscher ............................... 119/83 |
| 4,461,285 | 7/1984 | Courtin ................................. 601/137 |
| 4,463,485 | 8/1984 | Gueret .................................. 601/137 |
| 4,480,596 | 11/1984 | Shumiyashu ........................ 600/15 |
| 4,489,711 | 12/1984 | Latzke .................................. 600/15 |
| 4,549,532 | 10/1985 | Baermann ............................ 600/15 |
| 4,550,714 | 11/1985 | Talish et al. ......................... 600/14 |
| 4,757,804 | 7/1988 | Griffith et al. ....................... 600/13 |
| 4,798,194 | 1/1989 | Amishima ............................ 600/15 |
| 4,846,159 | 7/1989 | Anzai et al. ......................... 601/128 |
| 5,214,404 | 5/1993 | Yamaguchi .......................... 335/302 |
| 5,304,111 | 4/1994 | Mitsuno et al. ..................... 600/15 |
| 5,314,401 | 5/1994 | Tepper ................................. 600/15 |

FOREIGN PATENT DOCUMENTS

| | | |
|---|---|---|
| 5-23219 | 2/1993 | Japan . |
| 6-14813 | 1/1994 | Japan . |

OTHER PUBLICATIONS

C.N. Kobluk et al., "A Scintigraphic Investigation of Magnetic Field Therapy on the Equine Third Metacarpus", *Veterinary and Comparative Orthopaedics and Traumatology*, pp. 3-7 (1994).

*Primary Examiner*—Robert P. Swiatek
*Assistant Examiner*—Elizabeth Shaw
*Attorney, Agent, or Firm*—Pennie & Edmonds

[57] ABSTRACT

A hand-held grooming device grooms, massages, and provides magnetic therapy for animals. The device has a base that is configured to be hand-held. On the base, there is formed a grooming pad having projections adapted for grooming and massaging. The grooming pads are formed by either a plurality of parallely arranged strips each having magnetic properties or a single magnetic sheet. Each strip has its magnetic poles aligned uniformly so that it's longitudinal ends are polar opposites. Similarly, the opposite ends of the magnetic sheet have opposite magnetic poles.

18 Claims, 3 Drawing Sheets

THERAPEUTIC GROOMER

BACKGROUND

The present invention relates to hand-held therapeutic devices for grooming domesticated animals, particularly horses. More specifically, it relates to a groomer that provides magnetic therapy, manual massage, and grooming functions.

Massage therapy has been known to relieve muscle pains by improving blood circulation. Similarly, magnetic therapy has been shown to benefit the circulation of blood in humans and in animals. See for example "A Scintigraphic Investigation of Magnetic Field Therapy on the Equine Third Metacarpus", *Veterinary and Comparative Orthopaedics and Traumatology*, January 1994; U.S. Pat. No. 238,444 issued to Scott; U.S. Pat. No. 675,527 to Righter; U.S. Pat. No. 4,266,533 to Ryaby et al.; U.S. Pat. No. 4,480,596 to Shumiyashu; U.S. Pat. No. 4,489,711 to Latzke; U.S. Pat. Nos. 4,549,532; 4,550,714 to Talish et al.; U.S. Pat. No. 4,757,804 to Griffith et al.; U.S. Pat. No. 4,846,159 to Anzai et al.; U.S. Pat. No. 5,304,111 to Mitsuno et al.; and U.S. Pat. No. 5,314,401 to Tepper.

In U.S. Pat. No. 4,846,159, a hand-held massager provides magnetic therapy, using magnetized rotatable balls that have protruding teeth. The magnetic field lines run from one pole of a ball to its opposite pole, intersecting a subject's skin as it rotates. Thus, a magnetic field is applied to the tissues underlying the skin being massaged. While such a device provides a magnetic therapy, it cannot be used to groom and clean an animal's skin or hide.

U.S. Pat. Nos. 5,314,401; 4,757,804; 4,550,714; 4,480,596; and 4,266,533 contemplate using electromagnetic devices for treating living tissues and organs. These devices are typically left attached to a limb or the torso. They rely on a power supply and usually are not hand-held. And they cannot be used as a grooming implement.

U.S. Pat. Nos. 4,489,711; 4,549,532; and 5,304,111 contemplate using permanently magnetized pads and sheets to treat humans or animals. These devices typically have a flexible sheet impregnated with magnetic ferrite particles in various patterns. For example, the '711 patent discloses a rubbery sheet formed of magnetized stripes. The magnetic poles extend perpendicularly to the sheet's plane, in an alternating pattern. The '532 patent discloses a flexible rubbery sheet having predetermined patterns, such as concentrically, angularly, and radially arranged sectors. The magnetic particles in a given sector have a common polarity, providing the sheet with a patterned surface of sectors of alternating polarity. Again, the poles extend perpendicularly to the sheet's plane. And in the '111 patent, the flexible planar magnetic sheet has a regular repeating pattern of curved areas of alternating polarity. Again, the poles are arranged perpendicularly to the sheet's plane. These planar pads are designed to be left on the body part being treated. And they neither provide any physical therapeutic massage nor grooming functions.

In addition to physical training, magnetic therapy can be used to condition, promote healing of those overworked muscles, and keep animals in peak condition. In this regard, magnetized pads, such as ones sold under the trade name EQUINEPAD™, have been contemplated for treating horses. This product, like the ones used on humans, is generally planar and cannot provide physical massaging and grooming functions; its sole function is to supply a magnetic field over the area being treated.

In general, domesticated animals kept for riding and show require regular grooming to keep their coats clean and healthy. A variety of devices, such as grooming brushes, mitts as described in U.S. Pat. No. 840,328, curry combs, and one-piece neoprene brushes, as described in U.S. Pat. No. 4,343,265 have long been used to remove dirt, dandruff and loose hair from an animal's coat. But these prior art devices provide no therapeutic benefits, other than the ones derived from their grooming function.

U.S. Pat. Nos. 238,444 and 675,527 disclose a hand-held magnetic brush for treating hair and scalp. The brush base, where the metallic or non-metallic bristles are held, contains magnets. Rather than using them over one's or animal's body, these brushes are used principally for combing hair. And they don't provide any massaging function.

There is a need for a simple, economical grooming device that grooms, massages, and provide magnetic therapy, particularly for animals.

SUMMARY

The present invention is a hand-held grooming device which simultaneously grooms, massages, and provides magnetic therapy when used on animals, especially a horse. The present grooming base has a grip portion configured to be hand-held, a grooming pad adapted for grooming formed on one face of the base. The pad has a plurality of projections extending therefrom. At least the projections are magnetic. Unlike the flat magnetic sheets and pads found in the prior art, the grooming pad has a three-dimensional magnetic surface that comes into contact with the animal's coat. Because the grooming pad is magnetic and has a three-dimensional surface, it can provide both physical and magnetic massaging therapy.

The grooming pad is preferably defined by a plurality of longitudinal strips that are preferably aligned side-by-side in parallel. The strips each have a first longitudinal end and a second longitudinal end. The projections are preferably integrally formed with the strips. The strips are formed on one face and the grip portion is formed on the opposite face. The grip portion is preferably a strap that forms a loop with the base. This enables the user to conveniently slip a hand through the loop.

Although only the projections need to be magnetic, each strip is also magnetic to enhance the pad's magnetism. The longitudinal first ends, as well as the second ends, of the adjacent strips have opposite poles. Each strip preferably has a plurality of magnetic projections arranged in a single row, preferably forming projections that are aligned in rows and columns. And the grooming pad preferably provides a magnetic field on the order of about 400–1800 gauss.

Although the grooming pad is preferably formed from a somewhat flexible synthetic material, it is not intended to conform to every contour of an animal's body. Instead, it is adapted for cleaning the animal's coat of dirt, loose hair and skin, and other debris. It is also adapted to provide a fairly resilient surface for massaging the animal. The magnetized three-dimensional grooming projections are swept across the animal's body during grooming, which not only grooms it, but also massages it, both physically and magnetically.

BRIEF DESCRIPTION OF THE DRAWINGS

These and other features, aspects, and advantages of the present invention will become much more apparent from the following description, appended claims, and accompanying drawings where:

DETAILED DESCRIPTION

Figure 1:
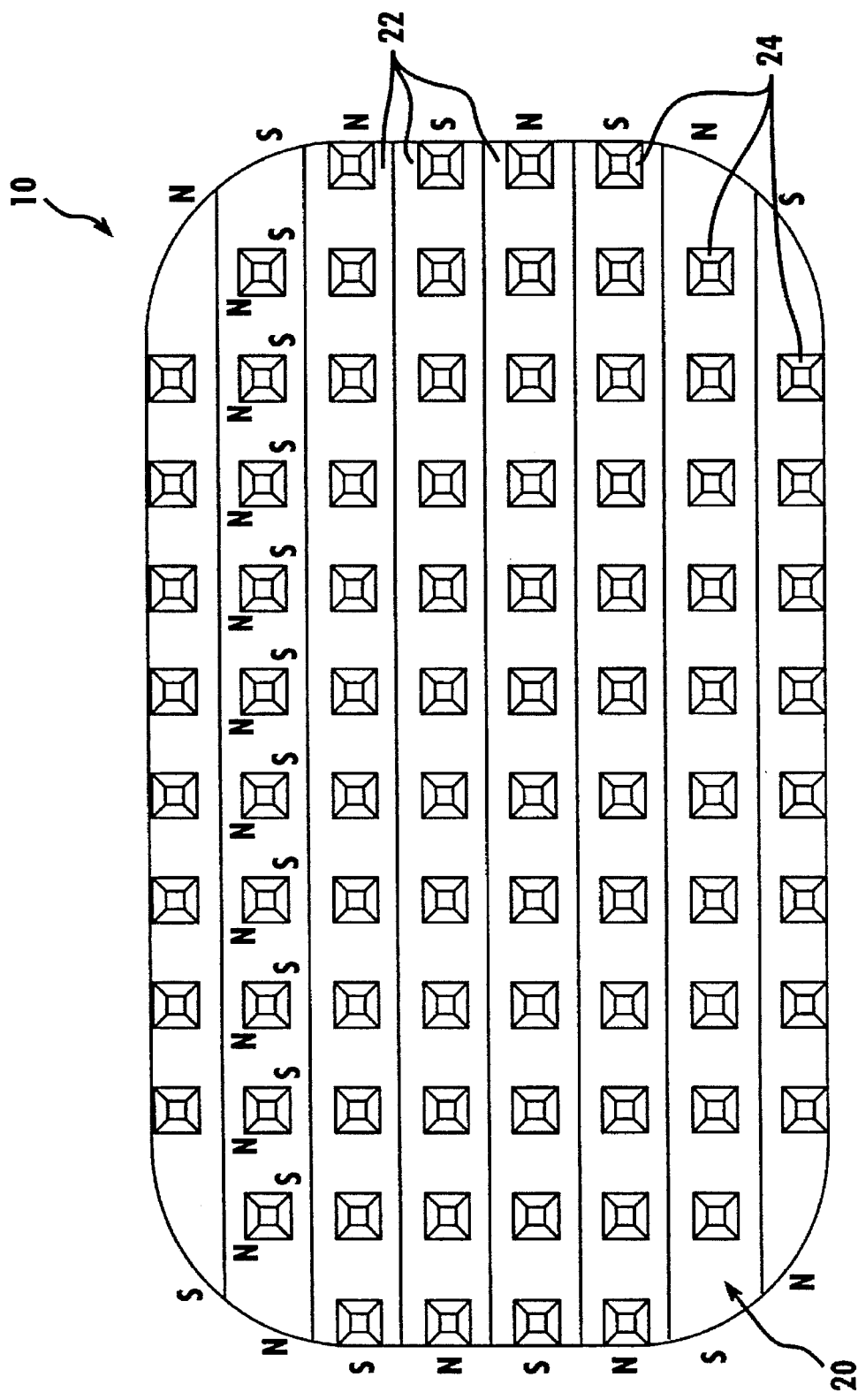
FIG. 1 is a bottom view of a groomer according to the present invention.

A groomer 10 contemplated in FIGS. 1–4 comprises a base or body 12 on which a handle or grip portion 14 is formed and a grooming pad 20. The handle 14 can be any conventional type, configured to be hand-held. The handle shown herein is a strap—either attached to or integrally formed with the base's opposing sides or face—forming a loop through which the user's hand can be placed. This function can also be served by a protrusion or the like (formed on the back face of the body) that the user can grab, or by contouring the brush base itself that can be grasped by the user. The grooming pad 20 is preferably attached to the base, at the side or face opposite the handle portion, by any conventional means, such as adhesive, screws, thermal bonding, or even VELCRO and guides, such as rails that enables the strip to be replaced.

The groomer base 12 is preferably formed from a relatively hard synthetic material, but is not a steadfast requirement; other non-magnetic materials such as wood and synthetic resin may also be used for this purpose. Magnetic material that would enhance the pad's magnetic strength can also be used. The base is preferably stiff, but provides some flexibility so that it can conform to the contours of the areas being groomed and massaged. The base, as shown, has an oval shape, but can have any other configuration, i.e., rectangular, circular, etc., suitable for grooming and massaging.

The grooming pad 20 preferably comprises strips 22 preferably aligned (side-by-side) in parallel rows, abutting adjacent strips. Although the strips are abutting, as shown in the drawings, they can also be arranged in non-abutting relationship. As shown, each strip 22 extends the entire length of the base, i.e., conform to the periphery configuration of the base. The strips 22 are preferably made of rubbery-flexible synthetic material suitable for grooming and massaging. Neoprene and rubber, for example, are suitable for this purpose. Each strip 22 is magnetic, which can be formed in several different conventional ways, such as by embedding the strip with permanent-magnetic ferrite particles or using a conventional flexible magnetic material. It is desirable to align the magnetic poles in a uniform direction so that the longitudinal ends of the strips are polar opposites, designated by the letters "N" (North) and "S" (South). See FIGS. 1 and 2. As shown in FIG. 1, the strips are arranged with the strip-ends' polarity alternating, so that the strip-ends' polarity of any one strip is opposite the strip-ends' polarity of any adjacent strip.

Figure 4:
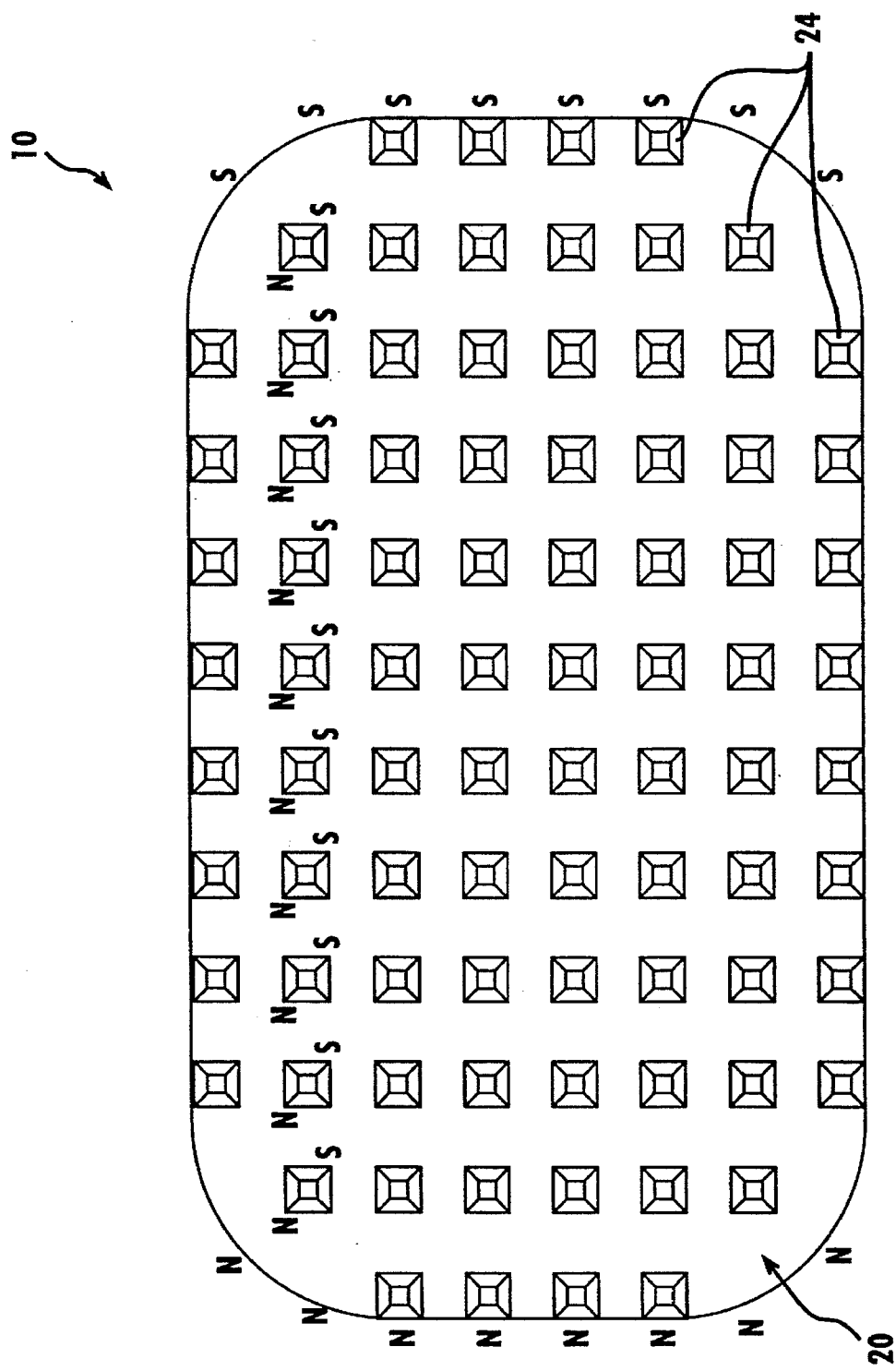
FIG. 4 is a bottom view of a groomer according to another embodiment of the present invention.

FIG. 4 is substantially similar to FIG. 1 except that the grooming pad in FIG. 4 can be formed of either a single sheet (as shown) or strips (as shown in FIG. 1). And the embodiment in FIG. 4 has the poles aligned all in a uniform direction so that the two opposing sheet ends have opposite poles.

The groomer according to the present invention preferably produces a magnetic strength on the order of 400–1800 gauss.

Figure 2:
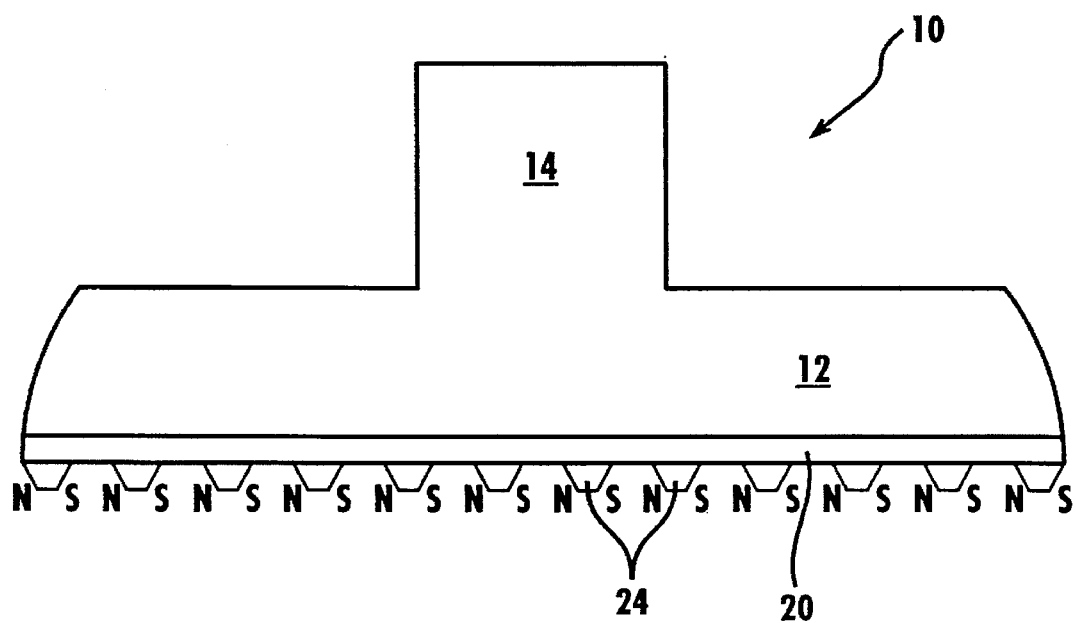
FIG. 2 is a side view of the groomer.
Figure 3:
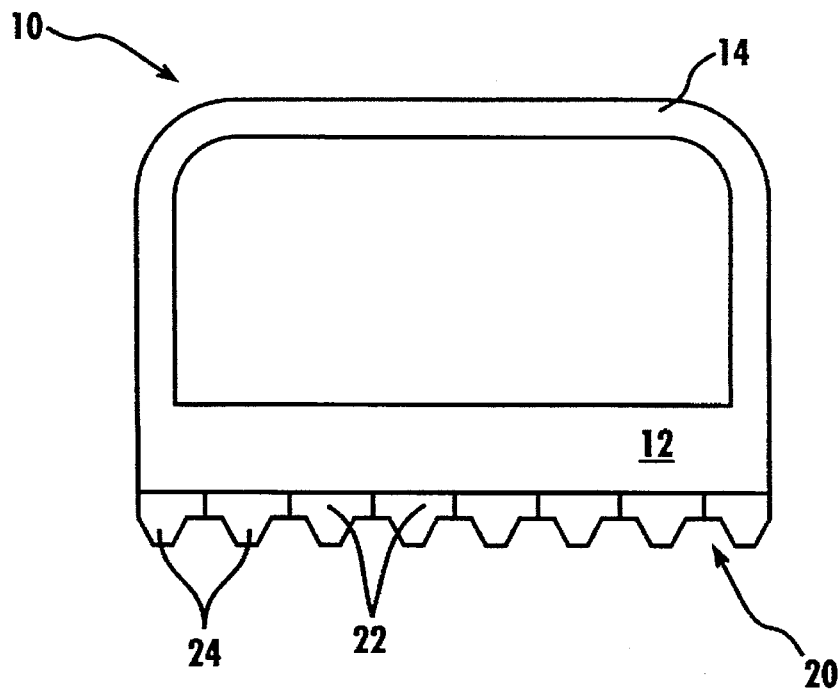
FIG. 3 is an end view of the groomer.

In the preferred embodiments, each strip (FIG. 1) or the sheet (FIG. 4) has a plurality of longitudinally spaced projections 24, such as teeth, nubs, configured for grooming and massaging. Preferably, the projections are equally sized and spaced, although they can be differently sized or spaced, or both if desired. They are also preferably laid in a single row along the length of each strip (FIG. 1). As shown in FIG. 1, the strips are aligned so that the projections 24 form straight rows and columns. Similarly, as shown in FIG. 4, the projections 24 preferably form straight rows and columns. The projections, however, can alternate in a checkered fashion if desired. And, as shown in FIG. 2, the projections are preferably pyramidal, with a rather blunt tip or truncated ends. Depending on the desired degree of massaging and hardness of the material used, however, the tips can be made sharp or blunt or a combination of both. FIG. 2 specifically shows a rectangular pyramidal projections, each having a rectangular base that narrows down to a blunt tip. Although not shown, the projections can have any other desired geometrical configuration, such as conical, hexagonal, triangular, oval shaped pyramid.

Preferably, the projections are integrally formed with the strip or the sheet, or attached to the strip or the sheet, via any conventional means, such as bonding, mechanical attachment (screw, bolt), in which case the projections should be magnetic (with proper polar orientation as shown in FIG. 1), or at least be magnetically conductive. The surface of a projection facing an end of the strip has the same polarity as that end. See FIG. 2. Because of this arrangement, the magnetic field extends from the two polar opposites, both within the same projection and the opposing sides of the adjacent projections (within the same strip). As a result, the magnetic field extends outwardly, in the direction that would extend inwardly into the muscles during grooming.

The purpose of the projections is to not only clean the animal's coat or fur (hair), but also massage, both physically and magnetically, as the grooming pad is drawn across the animal's body during the grooming process. During this process, the magnetic field from the pad penetrates into the animal's body.

In the aforementioned "A Scintigraphic Investigation of Magnetic Field Therapy on the Equine Third Metacarpus", it was reported that the placement of permanent magnetic pads on the equine metacarpus increases blood flow and metabolic activity. In general, the merits of employing a magnetized groomer for massaging and conditioning include increased blood flow to the area being massaged, overall increased circulation of the animal and stimulation of the surface tissue and muscle. It is believed that hand-held magnetic therapy adds a new dimension to the grooming process.

Given the disclosure of the present invention, one versed in the art would readily appreciate the fact that there can be other embodiments and modifications well within the scope and spirit of the disclosure set forth herein, but not specifically depicted and described. Accordingly, all expedient modifications readily attainable by one versed in the art from the disclosure set forth herein that are within the scope and spirit of the present invention are to be included as further embodiments of the present invention. The full scope of the present invention accordingly is to be defined in the appended claims.

What is claimed is:

1. A device for grooming an animal comprising:

a base having a grip portion configured to be hand-held;

a grooming pad adapted for grooming formed on one side of the base, said grooming pad having a plurality of non-movable projections extending therefrom, at least said projections being magnetic, each of said projections having a first face facing in a first direction and a second face facing in a second direction opposite said first direction, said first and second faces having opposite magnetic polarities, wherein said grooming pad is further adapted for massaging and providing magnetic therapy.

2. A device according to claim 1, wherein said grooming pad comprises a plurality of longitudinal strips, each said strip having a first longitudinal end and a second longitudinal end, with said projections integrally formed with said strips.

3. A device according to claim 2, wherein said base has a first face and a second face, said strips being formed on said first face and said grip portion formed on said second face.

4. A device for grooming an animal comprising:
 a base having a grip portion configured to be hand-held;
 a grooming pad adapted for grooming formed on one side of the base, said grooming pad having a plurality of non-movable projections extending therefrom, at least said projections being magnetic,
 wherein said grooming pad is further adapted for massaging and providing magnetic therapy,
 said grooming pad comprising a plurality of longitudinal strips, each said strip having a first longitudinal end and a second longitudinal end, with said projections integrally formed with said strips, and
 wherein each of said strips is also magnetic, with its longitudinal ends having polar opposite magnetic poles.

5. A device according to claim 3, wherein said grip portion is a strap.

6. A device according to claim 4, wherein said strips are parallely aligned side-by-side.

7. A device according to claim 6, wherein said longitudinal first ends as well as said longitudinal second ends of the adjacent strips have opposite magnetic poles.

8. A device according to claim 7, wherein each strip has a plurality of said projections arranged in a single row.

9. A device according to claim 1, wherein the magnetic field provided by said grooming pad has a strength between 400–1800 gauss.

10. A device according to claim 1, wherein said projections are aligned to form straight rows and columns.

11. A device according to claim 10, wherein said projections are integrally formed with said pad.

12. A device according to claim 1, wherein said grooming pad has two ends, and wherein said two ends have opposite magnetic poles.

13. A device for grooming an animal comprising:
 a base having a grip portion configured to be hand-held; and
 a grooming pad adapted for grooming formed on one side of the base, said grooming pad comprising
  a plurality of longitudinal magnetic strips, each of said strips having a first longitudinal end and a second longitudinal end, said longitudinal ends having polar opposite magnetic poles, and
  a plurality of non-movable magnetic teeth integrally formed with said strips and extending therefrom;
 wherein said grooming pad is further adapted for massaging and providing magnetic therapy.

14. A device according to claim 13 wherein each of said teeth has a first face facing in a direction of said first longitudinal end and a second face facing in a direction of said second longitudinal end, said first face and said first longitudinal end having the same magnetic polarity and said second face and said second longitudinal end having the same magnetic polarity.

15. A device for grooming an animal comprising:
 a base having a grip portion configured to be hand-held;
 a grooming pad formed on one side of the base said grooming pad having a plurality of magnetic teeth integrally formed with said grooming pad, said teeth having at least two planar side walls;
 wherein said grooming pad is further adapted for massaging and providing magnetic therapy, and wherein said grooming pad has two ends, and wherein said two ends have opposite magnetic poles.

16. A device for grooming an animal comprising:
 a base having a grip portion configured to be hand-held;
 a grooming pad formed on one side of the base, said grooming pad having a plurality of magnetic teeth integrally formed with said grooming pad, wherein
 each of said teeth has first face facing in a first direction and a second face facing in a second direction opposite to said first direction, said first and second faces having opposite magnetic polarities.

17. A device according to claim 16, wherein the magnetic field provided by said grooming pad has a strength between 400–1800 gauss.

18. A device according to claim 16, wherein said teeth are aligned to form straight rows and columns.

\* \* \* \* \*